(12) United States Patent
Honda

(10) Patent No.: US 7,762,947 B2
(45) Date of Patent: Jul. 27, 2010

(54) CAPSULE ENDOSCOPE AND CAPSULE ENDOSCOPE SYSTEM

(75) Inventor: Takemitsu Honda, Tokyo (JP)

(73) Assignee: Olympus Corporation, Tokyo (JP)

( * ) Notice: Subject to any disclaimer, the term of this patent is extended or adjusted under 35 U.S.C. 154(b) by 725 days.

(21) Appl. No.: 11/594,438

(22) Filed: Nov. 8, 2006

(65) Prior Publication Data

US 2007/0073105 A1    Mar. 29, 2007

Related U.S. Application Data

(63) Continuation of application No. PCT/JP2005/008421, filed on May 9, 2005.

(30) Foreign Application Priority Data

May 10, 2004   (JP)   ............................. 2004-139890

(51) Int. Cl.
 *A61B 1/04*   (2006.01)
(52) U.S. Cl. .................. 600/109; 600/118; 600/160; 348/68; 348/69
(58) Field of Classification Search ............. 600/109, 600/117, 118, 160, 178–181, 476–477; 348/65, 348/68–69, 74, 241, 243, 250
See application file for complete search history.

(56) References Cited

U.S. PATENT DOCUMENTS

| 6,654,054 | B1 * | 11/2003 | Embler .................. 348/241 |
| 6,724,418 | B1 * | 4/2004 | Takahashi ................. 348/65 |
| 7,023,479 | B2 * | 4/2006 | Hiramatsu et al. .......... 348/243 |
| 7,029,437 | B2 * | 4/2006 | Kobayashi ................ 600/180 |
| 7,247,135 | B2 * | 7/2007 | Iriyama .................. 600/181 |
| 7,452,328 | B2 * | 11/2008 | Homan et al. ............. 600/180 |
| 2002/0158976 | A1 | 10/2002 | Vni et al. |
| 2003/0081823 | A1 * | 5/2003 | Nonaka .................. 382/132 |
| 2003/0117491 | A1 | 6/2003 | Avni et al. |
| 2004/0027469 | A1 * | 2/2004 | Tsuruoka ................ 348/241 |
| 2004/0215059 | A1 * | 10/2004 | Homan et al. ............. 600/160 |

FOREIGN PATENT DOCUMENTS

| JP | H01-207032 | 8/1989 |
| JP | H01-250918 | 10/1989 |

(Continued)

OTHER PUBLICATIONS

Japanese Office Action dated Nov. 6, 2009 with translation.

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

A capsule endoscope, which is inserted into a subject and picking up an image inside the subject, includes an illuminating unit that illuminates an interior surface of the subject with illuminating light; an imaging unit that generates an electronic signal corresponding to incident light and outputs the electronic signal generated; a noise canceller that eliminates noise charges which are caused by dark current and accumulated in the imaging unit; and a timing controller that controls driving timing of the noise canceller so that the driving timing lays within a period after the imaging unit finishes an output operation of the electronic signals and before the illuminating unit starts to emit the illuminating light.

4 Claims, 7 Drawing Sheets

FOREIGN PATENT DOCUMENTS

| | | | |
|---|---|---|---|
| JP | 08065578 A * | 3/1996 | |
| JP | 11-253397 | 9/1999 | |
| JP | 2001-340324 | 12/2001 | |
| JP | 2003-070728 | 3/2003 | |
| WO | WO 02/080376 A2 | 10/2002 | |
| WO | WO 03/009739 A2 | 2/2003 | |
| WO | WO 2004082472 A1 * | 9/2004 | |

* cited by examiner

CAPSULE ENDOSCOPE AND CAPSULE ENDOSCOPE SYSTEM

CROSS-REFERENCE TO RELATED APPLICATIONS

This application is a continuation of PCT international application Ser. No. PCT/JP2005/008421 filed May 9, 2005 which designates the United States, incorporated herein by reference, and which claims the benefit of priority from Japanese Patent Application No. 2004-139890, filed May 10, 2004, incorporated herein by reference.

BACKGROUND OF THE INVENTION

1. Field of the Invention

The present invention relates to a capsule endoscope that is inserted into a subject and picks up an image inside the subject, and to a capsule endoscope system for the same.

2. Description of the Related Art

In a field of endoscopes, a swallowable type capsule endoscope has been proposed in recent years. The capsule endoscope has an imaging function and a radio transmission function. During a period from when the capsule endoscope is swallowed from a mouth of a subject for an observation (inspection) until when the capsule endoscope is naturally discharged, the capsule endoscope travels through inside a body cavity, i.e., inside organs such as a stomach and a small intestine, and sequentially images inside the organs, while following peristaltic motion of the organs.

Image data obtained inside a body by the capsule endoscope is sequentially transmitted to outside by radio transmission and stored in a memory provided outside, while the capsule endoscope travels through inside the body cavity. The subject can freely move during the period from when the capsule endoscope is swallowed until when the capsule endoscope is discharged, since the subject carries around a receiving device that has the radio transmission function and a memory function. After the capsule endoscope is discharged, a diagnosis can be made by a doctor or a nurse by displaying the image, which is based on the image data stored in the memory, of the organs on a display.

The imaging function provided in the capsule endoscope is realized by, for example, a predetermined optical system and an imaging element such as a charge-coupled device (CCD). Specifically, the capsule endoscope acquires the image inside the subject by converting incident light focused by the optical system to electronic signals.

However, the conventional capsule endoscope system has a problem in which it is not easy to acquire a high quality subject interior image. Specifically, in the conventional capsule endoscope, it is difficult to acquire the high quality subject interior image due to difficulties in an adjustment of illumination luminance of the capsule endoscope and presence of noise components in acquired image data. Hereinafter, the problem is described in details.

The conventional capsule endoscope has a problem in which it is not easy to adjust illumination light intensity of a light emitting diode (LED). Since the capsule endoscope needs to be miniaturized to a size insertable into the subject, it is preferred also to simplify a circuit installed in the capsule. Further, since the capsule endoscope needs to be driven for, for example, substantially 8 hours from when the capsule endoscope is inserted into the subject until when the capsule endoscope is discharged, a controlling circuit and the like provided in the capsule endoscope is required to have low power consumption.

Therefore, it is not realistic at least at the present moment to install a photochromatic mechanism, which is provided, for example, in a digital camera, in the capsule endoscope, so that it is necessary to provide a photochromatic mechanism specialized for the capsule endoscope. However, among the photochromatic mechanism proposed at the present moment, a photochromatic mechanism suitable for a use condition of the capsule endoscope does not necessarily exist.

A problem in which the noise components due to dark current are included in the image data will be described. The dark current is a current component caused independent of incident light, and caused due to a mechanism of an imaging element such as the CCD. The noise components are mixed into an acquired image data corresponding to an amount of the dark current.

FIG. 7 is a schematic graph of one example of temperature dependency of the dark current. As shown in FIG. 7, strength of the dark current tends to monotonously increase as the temperature rises, and the noise components caused due to the dark current increase along with the rise in environmental temperature.

Since the capsule endoscope performs an imaging operation inside the subject, the environmental temperature of the capsule endoscope becomes approximately 38° C. (Celsius). When the imaging element such as the CCD is used under such a temperature condition, the dark current increases to substantially 3 to 4 times an amount under a room temperature (for example, 20° C.). Therefore, when the imaging operation is performed by using the imaging element provided in the capsule endoscope, the amount of the dark current increases compared to when a normal imaging device is used, and the quality of the image is largely affected.

A configuration in which an imaging is performed while cooling the CCD to eliminate the influence of the dark current has been proposed, and some have already put the configuration into practical use. However, to install the cooling mechanism in the capsule endoscope is not appropriate since the cooling mechanism consumes large electric power, and currently, other alternative units do not exist.

SUMMARY OF THE INVENTION

A capsule endoscope according to one aspect of the present invention is inserted into a subject and picking up an image inside the subject, and includes an illuminating unit that illuminates an interior surface of the subject with illuminating light; an imaging unit that generates an electronic signal corresponding to incident light and outputs the electronic signal generated; a noise canceller that eliminates noise charges which are caused by dark current and accumulated in the imaging unit; and a timing controller that controls driving timing of the noise canceller so that the driving timing lays within a period after the imaging unit finishes an output operation of the electronic signals and before the illuminating unit starts to emit the illuminating light.

A capsule endoscope system according to another aspect of the present invention includes a capsule endoscope that is inserted into a subject, the capsule endoscope picking up an image inside the subject and radio transmitting a radio signal including image data to outside; and a receiving device that receives the radio signal transmitted from the capsule endoscope. The receiving device includes a receiving antenna unit that receives the radio signal transmitted from the capsule endoscope, and an external device that performs a predetermined processing on the radio signal received by the receiving antenna unit. The capsule endoscope includes an illuminating unit that illuminates an interior surface of the subject with illuminating light, an imaging unit that includes a photoelectric transducer, and outputs an electronic signal corresponding to incident light, a noise canceller that eliminates noise charges which are caused due to dark current and accumulated in the imaging unit, a timing controller that controls driving timing of the noise canceller so that the driving timing lays within a period after the imaging unit finishes an output operation of the electronic signal and before the illuminating unit starts to emit the illuminating light, and a radio unit that transmits the radio signal including the image data picked up by the imaging unit to outside.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Embodiments of a capsule endoscope system according to the present invention will be described below. It should be noted that the accompanying drawings are merely schematic, and relation between width and thickness of each portion, thickness ratio of one portion to another, and the like may be different in an actual apparatus and a system. The dimensional relations and the ratio may be different from one drawing to another.

Figure 1:
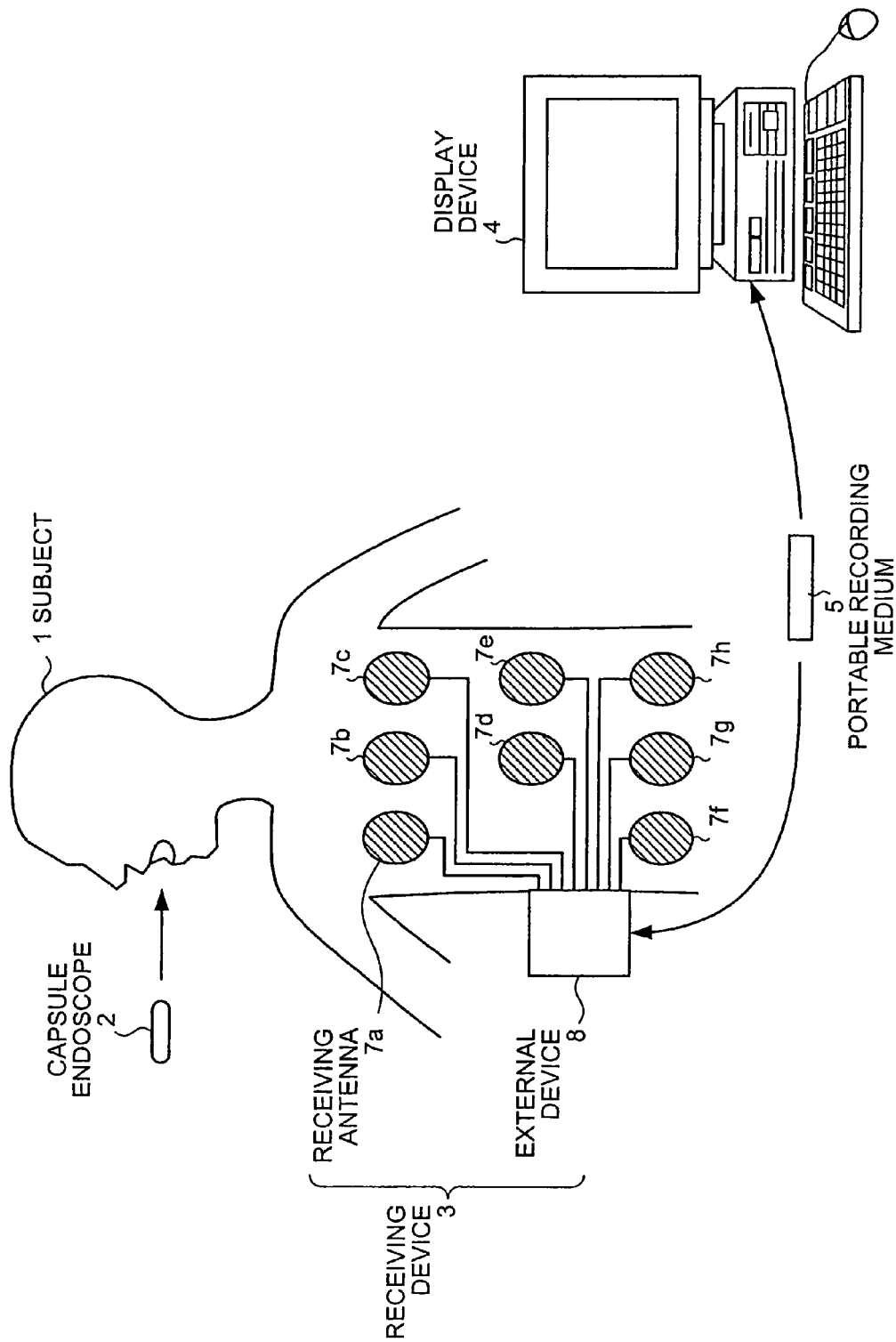
FIG. 1 is a schematic drawing of an overall configuration of a capsule endoscope system according to an embodiment.

FIG. 1 is a schematic drawing of an overall configuration of the capsule endoscope system according to the present embodiment. The capsule endoscope system according to the present embodiment has a capsule endoscope 2, a receiving device 3, a display device 4, and a portable recording medium 5. The capsule endoscope 2 is inserted into a subject 1 to pick up a subject interior image, and radio transmits a picked up data to outside. The receiving device 3 detects a position of the capsule endoscope 2 inside the subject 1. The display device 4 displays contents of image data received by the receiving device 3. The portable recording medium 5 transfers information between the receiving device 3 and the display device 4.

The display device 4 serves to display the subject interior image picked up by the capsule endoscope 2, and the display device 4 has a configuration such as a work station displaying the image based on data acquired through the portable recording medium 5. Specifically, the display device 4 may directly display the image by a cathode ray tube (CRT) display, a liquid crystal display, and the like, or may output the image to other medium such as a printer and the like.

The portable recording medium 5 is detachable with respect to an external device 8 described later and the display device 4, and the portable recording medium 5 is capable of outputting and recording the information when the portable recording medium 5 is attached to the external device 8 or the display device 4. Specifically, while the capsule endoscope 2 travels inside the subject 1, the portable recording medium 5 is attached to the external device 8 and records the information related to the position of the capsule endoscope 2. After the capsule endoscope 2 is discharged from the subject 1, the portable recording medium 5 is removed from the external device 8 and attached to the display device 4, and the recorded data is read by the display device 4. Unlike when the external device 8 and the display device 4 are connected to each other through a cable, the subject 1 can freely move while the capsule endoscope 2 travels inside the subject 1 since the data are transferred between the external device 8 and the display device 4 by the portable recording medium 5 such as a Compact Flash (registered trademark) memory and the like.

The receiving device 3 serves to receive the image data radio transmitted from the capsule endoscope 2, and to record the image data in the portable recording medium 5 after performing predetermined processing, if necessary, on the image data. Specifically, the receiving device 3 has receiving antennas 7a to 7h and the external device 8, and receives radio signals, which are transmitted from the capsule endoscope 2, through any of the receiving antennas 7a to 7h as well as outputs the image data to the portable recording medium 5 after performing a processing such as an extraction of the image data from the radio signals.

The capsule endoscope 2 will be described. The capsule endoscope 2 has a capsule-like exterior shape shown in FIG. 1, and is formed with predetermined elements arranged inside the capsule. For example, the capsule that forms the capsule endoscope 2 may be a spheroid. However, in the present embodiment, it is not necessary to consider the shape of the capsule as being specifically restricted, and an arbitrary shape may be used as long as the shape is swallowable by the subject 1.

Figure 2:
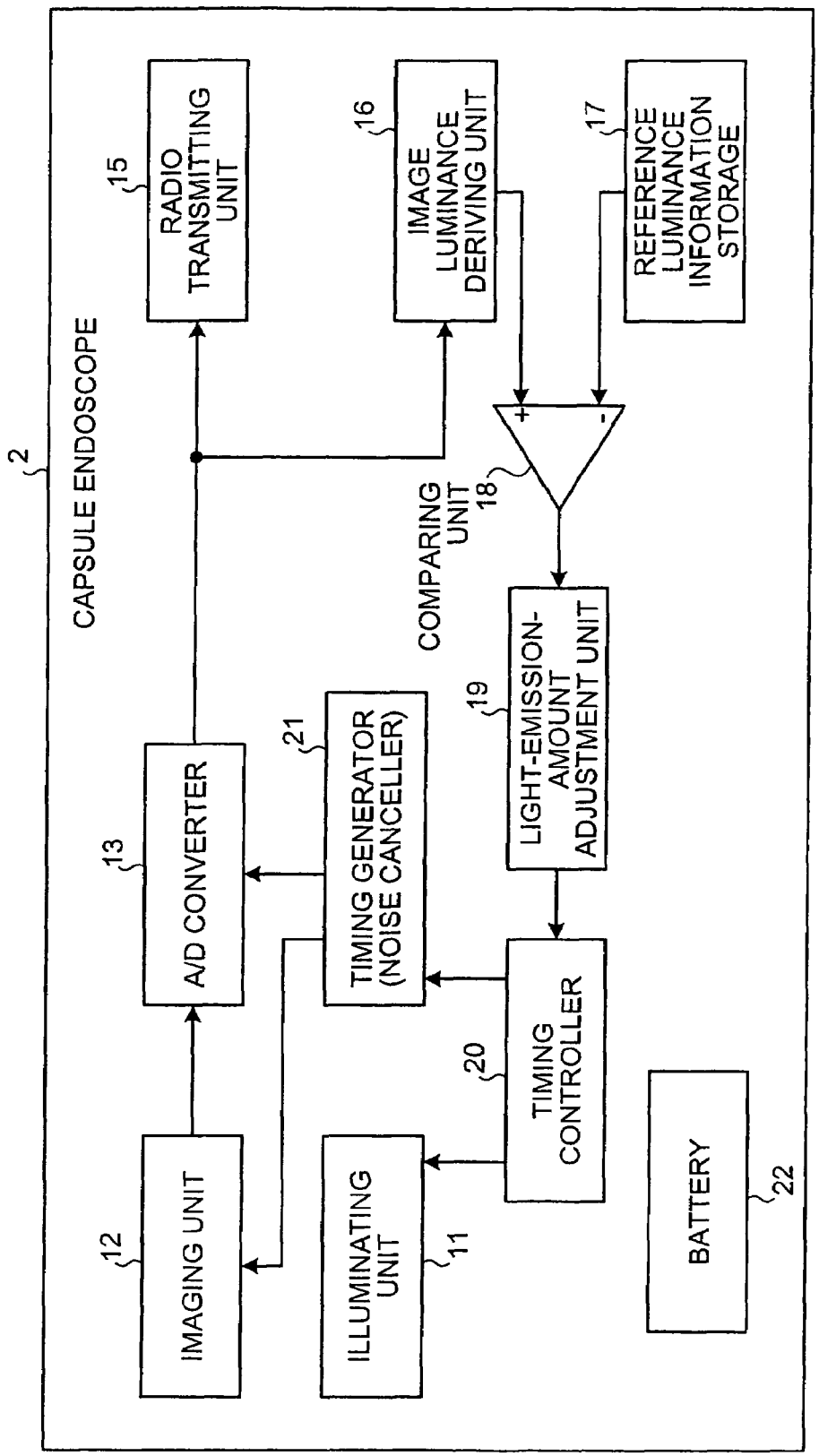
FIG. 2 is a block diagram of a configuration of a capsule endoscope provided in the capsule endoscope system.

FIG. 2 is a block diagram of an interior configuration of the capsule endoscope 2. The capsule endoscope 2 has a fist mechanism that picks up the subject interior image and the like, a second mechanism that adjusts intensity of the illuminating light when the subject interior image is picked up, and a third mechanism that determines driving timing of each element provided in the capsule endoscope 2. Hereinafter, each configuration of each mechanism and the like is described.

As shown in FIG. 2, the capsule endoscope 2 according to the present embodiment has a mechanism that picks up the subject interior image and transmits the picked up subject interior image to outside, as the first mechanism. The capsule endoscope 2 has an illuminating unit 11, an imaging unit 12, an A/D converter 13, and a transmitting unit 15. The illuminating unit 11 illuminates inside the subject 1 with predetermined illuminating light. The imaging unit 12 receives reflected light of the illuminating light output from the illuminating unit 11, and outputs analog electronic signals corresponding to intensity of the incident light. The A/D converter 13 converts the analog electronic signals output from the imaging unit 12 into digital electronic signals. The transmitting unit 15 performs a necessary processing on the digital electronic signals output from the A/D converter 13, and radio transmits the processed digital electronic signals to outside.

The illuminating unit 11 serves to output the illuminating light illuminating inside the subject 1, and the illuminating unit 11 allows the imaging unit 12 to pick up the subject interior image by outputting the illuminating light. Specifically, the illuminating unit 11 is formed with, for example, an emission mechanism such as an LED and a driving controlling circuit of the emission mechanism. The illuminating unit 11 has a function of performing an emission operation at a time point set by a timing controller 20 described later.

The imaging unit 12 serves to pick up the image inside the subject 1. Specifically, the imaging unit 12 has an optical system that focuses the incident light, and has a function of picking up the image inside the subject 1 by outputting the electronic signals corresponding to the intensity of the incident light focused by the optical system.

Figure 3:
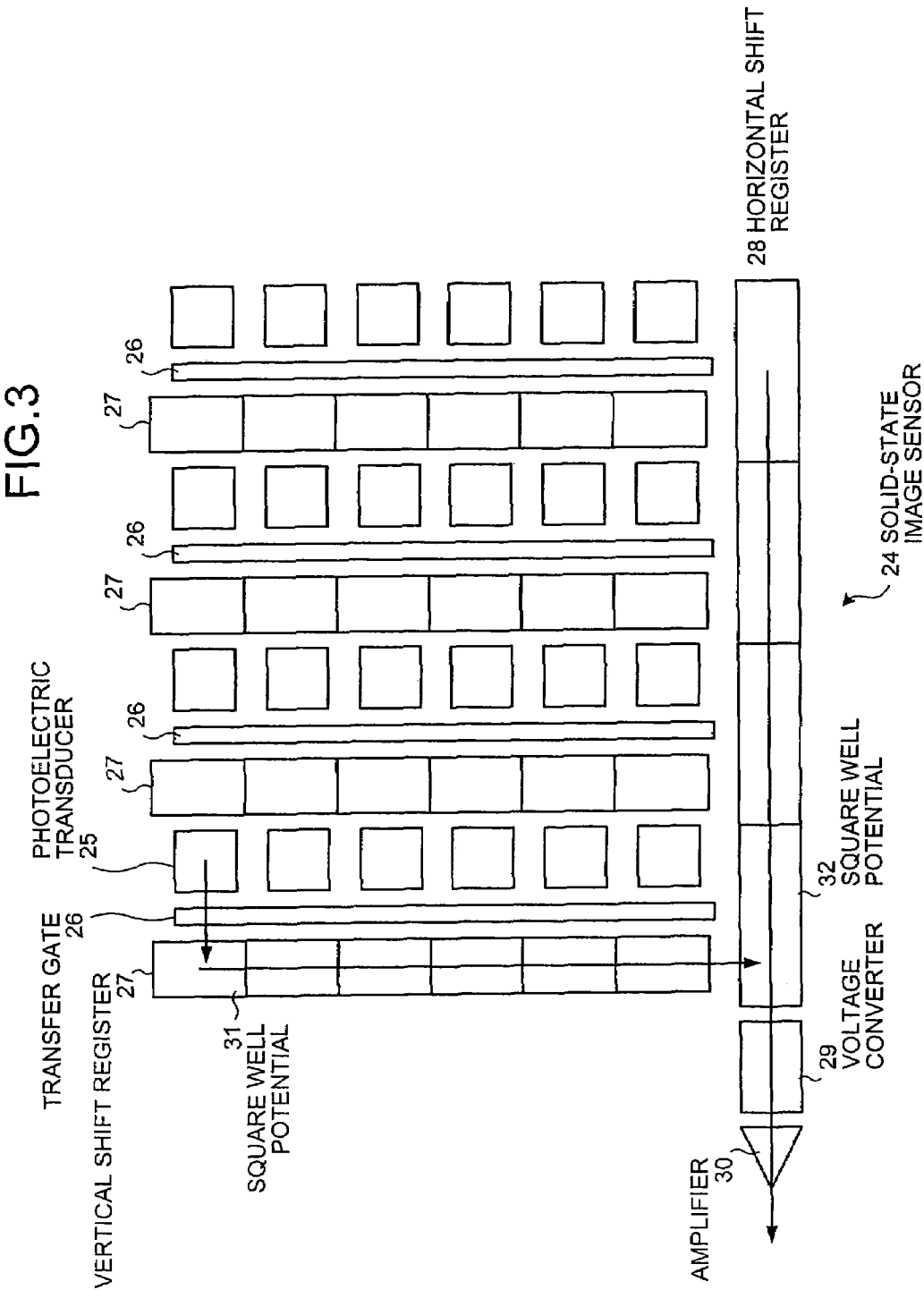
FIG. 3 is a schematic drawing of a configuration of one example of a solid-state image sensor that forms an imaging unit provided in the capsule endoscope.

FIG. 3 is a schematic drawing of a configuration of a solid-state image sensor 24 formed with a so called interline-type CCD element, and FIG. 3 is an example of an imaging element that forms the imaging unit 12. The solid-state image sensor 24 shown in FIG. 3 has plural photoelectric transducers 25, plural transfer gates 26, plural vertical shift registers 27, a horizontal shift register 28, a voltage converter 29, and an amplifier 30. The photoelectric transducers 25 are arranged in a matrix shape. The transfer gates 26 and the vertical shift registers 27 are extended in a column direction of the matrix of the photoelectric transducers 25, and arranged corresponding to number of rows. The horizontal shift register 28 is arranged at a downstream side of an output direction of charges of the vertical shift registers 27, and extended in a row direction. The voltage converter 29 converts charges output from the horizontal shift register 28 to voltage signals. The amplifier 30 amplifies the voltage signals output from the voltage converter 29. In the solid-state image sensor 24, it is not necessary to restrictively interpret the number of rows and columns of the matrix of the photoelectric transducers 25 to the numbers of rows and columns shown in FIG. 3, and practically, the numbers of rows and columns of the matrix are determined according to number of pixels of the picked up image.

The photoelectric transducers 25 serve to generate electronic signals corresponding to intensity of the incident light. The photoelectric transducers 25 are formed with, for example, photodiodes, and have a function of accumulating charges corresponding to the incident light.

The transfer gates 26 serve to control the charge transfer from the photoelectric transducers 25 to the vertical shift registers 27. Specifically, the transfer gates 26 have potentials that correspond to potentials applied by electrodes (not shown), and the charges stored in the photoelectric transducers 25 are transferred to the vertical shift registers 27 side according to the changes in the potentials.

The vertical shift registers 27 serve to shift the charges output from the photoelectric transducers 25 in the column direction. Specifically, the vertical shift registers 27 are configured by electrodes (not shown) controlling square well potentials 31 and potentials of the square well potentials 31 arranged according to the number of rows, and the vertical shift registers 27 have a function of shifting the charges transferred from the photoelectric transducers 25 in the column direction and outputting to the horizontal shift register 28, by sequentially changing the potentials of the square well potentials 31.

The horizontal shift register 28 serves to transfer the charges in the row direction. Specifically, the horizontal shift register 28 has square well potentials 32 corresponding to the number of rows of the matrix of the photoelectric transducers 25, and has a function of sequentially outputting the charges to the voltage converter 29 by sequentially controlling the potentials of the square well potentials 32.

The transmitting unit 15 serves to radio transmit image data, which is obtained through the imaging by the imaging unit 12 and converted to digital signals by the A/D converter 13. Specifically, the transmitting unit 15 has, for example, a transmitting circuit and a transmitting antenna. The transmitting circuit generates radio signals by performing a modulation processing and the like, if necessary, on the image data. The transmitting antenna serves to transmit the generated radio signals to outside.

The capsule endoscope 2 has a mechanism of adjusting the emission amount of the illuminating unit 11, as the second mechanism. Specifically, the capsule endoscope 2 has an image luminance deriving unit 16, a reference luminance information storage 17, a comparing unit 18, and a light-emission-amount adjustment unit 19. The image luminance deriving unit 16 derives image luminance of the image picked up by the imaging unit 12 based on the digital signals output from the A/D converter 13. The reference luminance information storage 17 acquires information related to predetermined reference luminance. The comparing unit 18 compares the image luminance with the reference luminance. The light-emission-amount adjustment unit 19 adjusts the emission amount of the illuminating unit 11 based on a comparison result of the comparing unit 18.

The image luminance deriving unit 16 serves to derive the image luminance of the image picked up by the imaging unit 12. The image luminance deriving unit 16 has a function of deriving average luminance of a single pixel by adding luminance of each pixel constituting the picked up image data and dividing the added result by the number of pixels. To implement the function, the image luminance deriving unit 16 has, for example, a detecting circuit.

The reference luminance information storage 17 stores information on preliminarily determined reference luminance. Specifically, the reference luminance information storage 17, for example, has a function of determining the reference luminance and storing information corresponding to the reference luminance. The reference luminance is set to a level that allows an operator to visually recognize the image content easily according to display ability of the display device 4. In the present embodiment, the reference luminance information storage 17 stores voltage value corresponding to the reference luminance as the reference luminance information, and specifically, the reference luminance information storage 17 has a constant voltage source that outputs the voltage value corresponding to the reference luminance.

The comparing unit 18 serves to compare the image luminance derived at the image luminance deriving unit 16 with the reference luminance stored in the reference luminance information storage 17, and to output the comparison result to the light-emission-amount adjustment unit 19. An arbitrary relationship may be used as the comparison result output by the comparing unit 18 as long as the arbitrary relationship corresponds to a correlation between the image luminance and the reference luminance. In the present embodiment, a magnitude correlation between the image luminance and the reference luminance is simply used as the comparison result derived by the comparing unit 18.

The light-emission-amount adjustment unit 19 serves to adjust light intensity of the illuminating light output from the illuminating unit 11 based on the comparison result acquired by the comparing unit 18. Specifically, the light-emission-amount adjustment unit 19 has a function of changing an output time of the illuminating light output from the illuminating unit 11 based on the comparison result derived by the comparing unit 18, and outputting information relating to the changed output time to the timing controller 20.

As a configuration to adjust the emission amount, it is proposed to adjust current supplied to the LED constituting the illuminating unit 11, for example, instead of adjusting the output time of the illuminating light. The above configuration or the like may be used to adjust the emission amount. However, in the present embodiment, from perspective of suppressing increase in power consumption and simplifying a control algorithm, emission luminance of a light-emitting element such as the LED provided in the illuminating unit 11 is not changed and the emission amount is adjusted by changing the emission time. An arbitrary algorithm may be employed to derive the output time of the illuminating light at the light-emission-amount adjustment unit 19 as long as the arbitrary algorithm adjusts the output time so as to decrease a difference between the reference luminance and the image luminance. However, in the present embodiment, to realize a simple configuration and the like, the output time of the illuminating light is uniformly decreased by a predetermined time when the image luminance exceeds the reference luminance and the output time of the illuminating light is uniformly increased by a predetermined time when the image luminance is below the reference luminance, corresponding to the configuration in which the comparing unit 18 simply outputs the magnitude correlation.

Furthermore, the capsule endoscope 2 has a mechanism that determines driving timing of each element, as the third mechanism. Specifically, the capsule endoscope 2 has a timing controller 20 and a timing generator 21. The timing controller 20 controls operation timing of each element. The timing generator 21 supplies the driving timing and the like to the imaging unit 12 and the A/D converter 13 based on the control of the timing controller 20. Further, the capsule endoscope 2 has a battery 22 that serves to supply driving power to each element.

The timing generator 21 serves to supply the driving timings to the imaging unit 12 and the A/D converter 13 as well as to output a shutter pulse (reset pulse) for eliminating noise components caused by the dark current. Specifically, the timing generator 21 supplies the driving timings of the imaging unit 12 and the A/D converter 13 as well as supplies the shutter pulse to the imaging unit 12, based on a command from the timing controller 20.

The elimination of the noise components will be described simply. As described with respect to the conventional art, when the imaging unit 12 has the photoelectric transducers 25, charges caused by the dark current are accumulated even while the illuminating light is not emitted from the illuminating unit 11, i.e., even while the light is not incident on the solid-state image sensor 24. Since the charges remain, components caused by the dark current, which has no relation to the incident light, are included in the charges output to outside from the photoelectric transducers 25, which are arranged in the matrix shape, after the imaging operation, and the image quality decreases.

Hence, in the present embodiment, the charges that are caused by the dark current and function as the noise components are eliminated before an output operation of the illuminating light emitted by the illuminating unit 11, as described in details later. Specifically, the timing generator 21 supplies the shutter pulse (reset pulse) to the imaging unit 12. Since the shutter pulse is supplied, predetermined potentials are, for example, supplied to the entire photoelectric transducers 25 and the charges accumulated by the dark current are discharged. Consequently, the timing generator 21 in the present embodiment functions as the noise canceller, and the timing generator 21 supplies the shutter pulse to the imaging unit 12 with predetermined timing commanded by the timing controller 20 to eliminate the noise components.

The timing controller 20 will be described. The timing controller 20 serves to determine operation timings of the illuminating unit 11, the imaging unit 12, the A/D converter 13, the image luminance deriving unit 16, and the like based on the output from the light-emission-amount adjustment unit 19. Specifically, the elements have a configuration in which the elements are driven according to the pulses output from the timing controller 20 or driven according to the pulses output from the timing generator 21 based on the control of the timing controller 20. In the present embodiment, the timing controller 20 controls the operation timings of the elements by controlling the rising edge and falling edge of the pulses.

Figure 4:
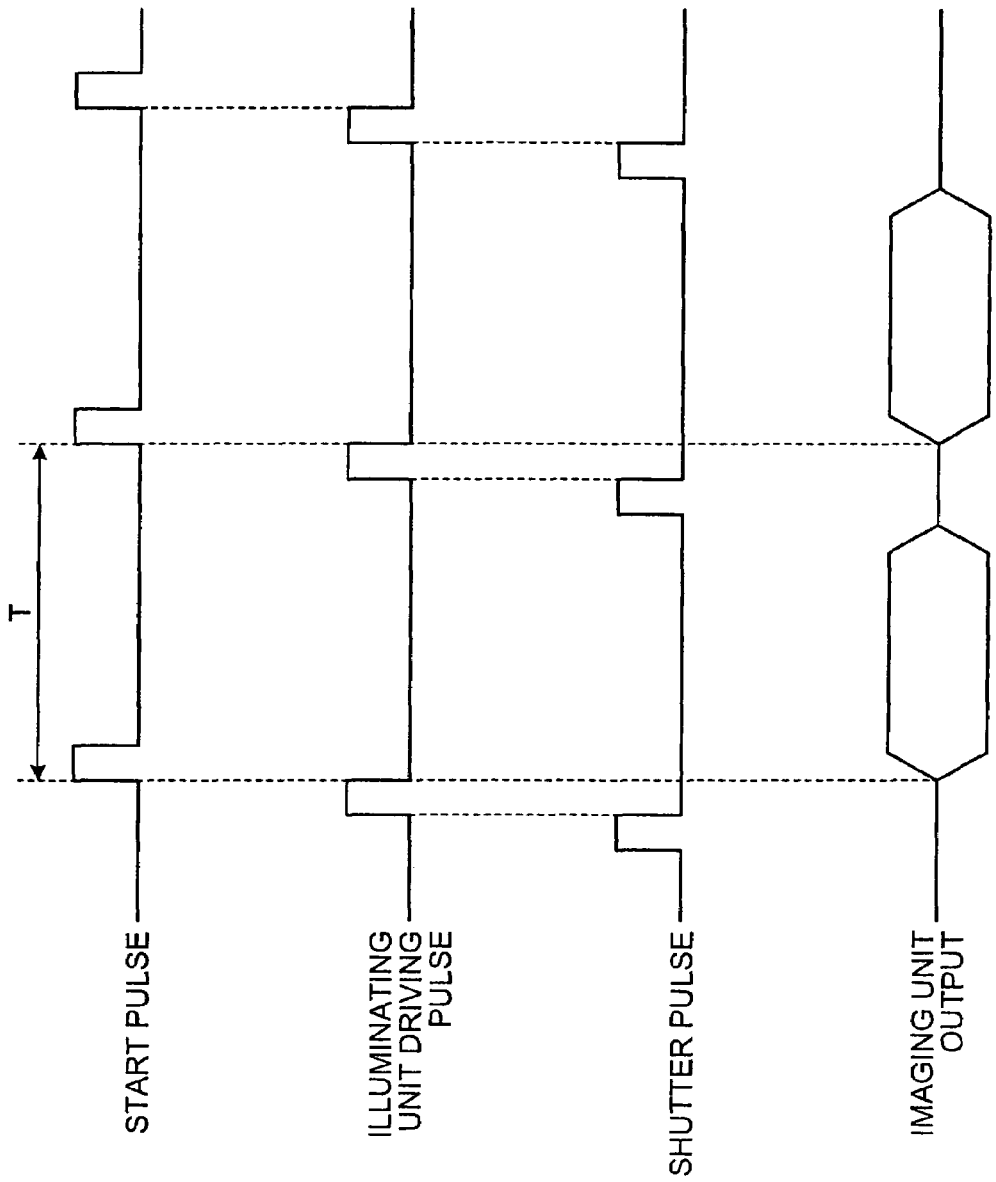
FIG. 4 is a timing chart of supplying timing, which is controlled by a timing controller provided in the capsule endoscope, of pulses.

FIG. 4 is a timing chart of supplying timings of the pulses controlled by the timing controller 20. First, a start pulse is generated under the control of the timing controller 20. The start pulse determines a starting of the imaging operation, i.e., starting time of an operation during which the charges accumulated in the photoelectric transducers 25 are output by the vertical shift registers 27 and the horizontal shift register 28. As shown in FIG. 4, an interval between the start pulses defines an imaging period T necessary to acquire one image. In response to the supply of the start pulse, the solid-state image sensor 24 transfers the charges accumulated in the photoelectric transducers 25 to the vertical shift registers 27 and outputs the analog electronic signals corresponding to the picked up image by operations of the vertical shift registers 27, the horizontal shift register 28, and the like. In synchronization with the output of the solid-state image sensor 24, the A/D converter 13 performs the processing, and the image data formed by the digital electronic signals is generated.

Further, an illuminating unit driving pulse that defines the driving timing of the illuminating unit 11 is supplied in the late imaging period, i.e., right before the start pulse that defines the starting of the next imaging period is supplied. In the present embodiment, the time to start driving the illuminating unit 11 is set on the rising edge of the illuminating unit driving pulse, whereas the time to stop driving the illuminating unit 11 is set on the falling edge of the illuminating unit driving pulse. The illuminating unit 11 is operated according to the illuminating unit driving pulse, and in the example shown in FIG. 4, the illuminating unit 11 outputs the illuminating light right before the start pulse is supplied, i.e., right before the transferring of the charges in the solid-state image sensor 24 is started.

Furthermore, in the late imaging period, the shutter pulse is supplied. In one imaging period, the shutter pulse is supplied at least after the imaging unit finishes data output operation and before the illuminating unit 11 starts to be driven, and in the example shown in FIG. 4, the supplying timing of the shutter pulse is controlled so that the rising edge of the illuminating unit driving pulse coincides with the falling edge of the shutter pulse.

The emission amount adjusting operation performed by the light-emission-amount adjustment unit 19 and a control performed by the timing controller 20 to change the pulse supplying timing based on the output from the light-emission-amount adjustment unit 19 will be described. The timing controller 20 basically controls the supply of the pulses shown in FIG. 4, though the timing controller 20 also has a function of changing the supplying timings of respective pulses according to an output value of the light-emission-amount adjustment unit 19. Hence, as described hereinbefore, the light-emission-amount adjustment unit 19 has a mechanism to adjust the emission amount by changing the output time of the illuminating light output from the illuminating unit 11. Therefore, it is necessary to lengthen pulse width of the illuminating unit driving pulse as well as to change supplying timings of other pulses shown in FIG. 4, to output the illuminating light with the emission amount adjusted by the light-emission-amount adjustment unit 19. Thus, the timing controller 20 controls the changes in the supplying timings of the pulses based on the output of the light-emission-amount adjustment unit 19.

Figure 5:
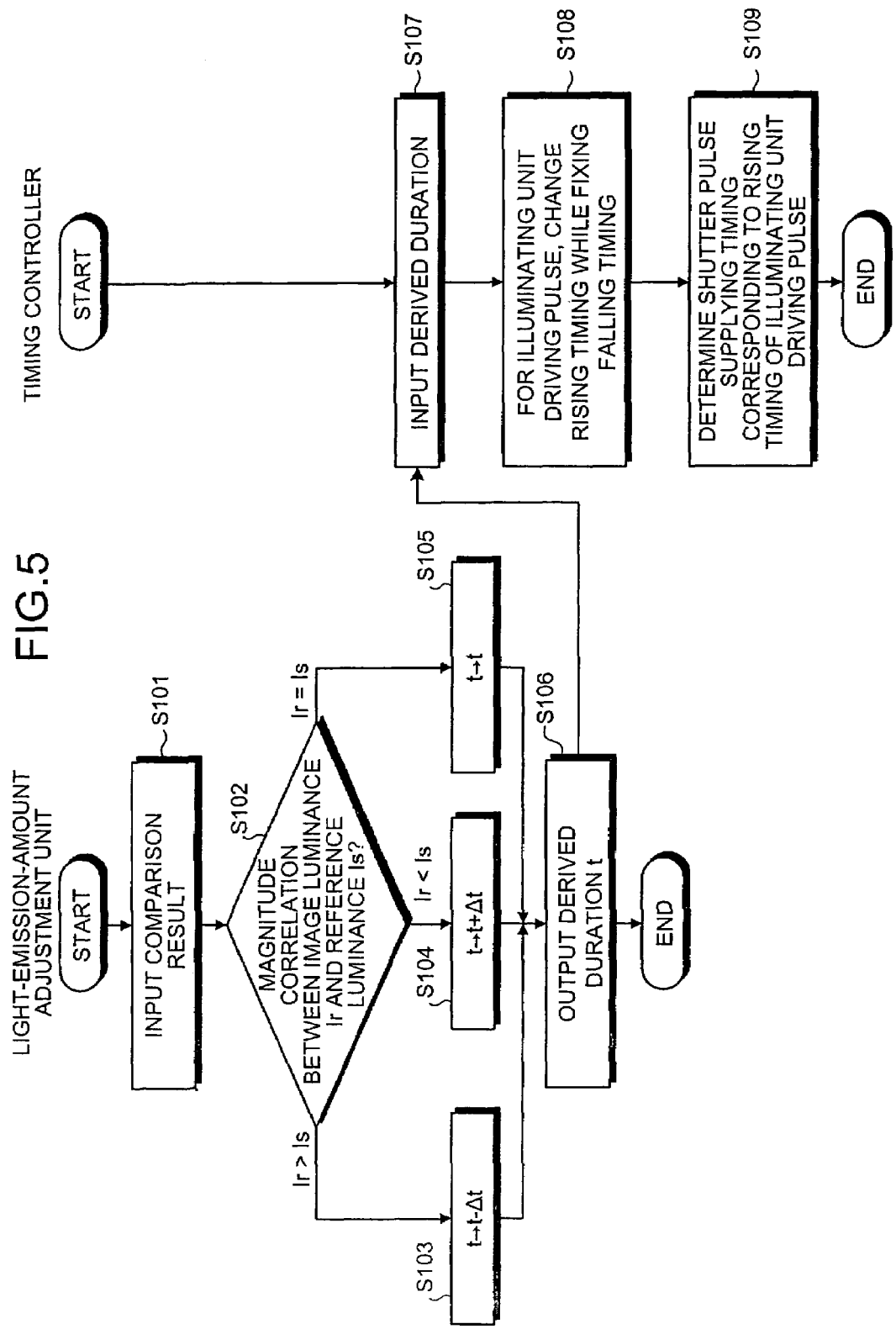
FIG. 5 is a flowchart for illustrating an operation of a light-emission-amount adjustment unit and the timing controller that are provided in the capsule endoscope.

FIG. 5 is a flowchart of the emission amount adjusting operation performed by the light-emission-amount adjustment unit 19, and the control performed by the timing controller 20 to change the pulse supplying timing subsequently to the emission amount adjusting operation. As shown in FIG. 5, the light-emission-amount adjustment unit 19 inputs the comparison result derived by the comparing unit 18 (step S101), and determines the magnitude correlation between the image luminance and the reference luminance based on the comparison result (step S102). When the image luminance exceeds the reference luminance (step S102, Ir>Is), the pulse width t of the illuminating unit driving pulse are changed to t−Δt (step S103). When the image luminance is below the reference luminance (step S102, Ir<Is), the pulse width t of the illuminating unit driving pulse is changed to t+Δt (step S104). Furthermore, when the image luminance and the reference luminance are equal to each other (step S102, Ir=Is), the pulse width t of the illuminating unit driving pulse is maintained at the same length (step S105). Then, the pulse width of the illuminating unit driving pulse determined at each of steps S103, S104, and S105 is output to the timing controller 20 (step S106).

An operation of the timing controller 20 will be described. First, the timing controller 20 receives a specific value of the pulse width of the illuminating unit driving pulse output from the light-emission-amount adjustment unit 19 (step S107). Then, the timing controller 20 shifts the rising edge of the illuminating unit driving pulse while keeping the falling edge of the illuminating unit driving pulse at the current point so that the pulse width of the illuminating unit driving pulse comes to take the received value (step S108). Thereafter, the timing controller 20 changes the timing of the rise and the fall of the shutter pulse following the shift of the rising edge of the illuminating unit driving pulse so that the falling edge of the shutter pulse coincides with the rising edge of the illuminating unit driving pulse (step S109). Thus, in accordance with the change in the output time of the illuminating light from the illuminating unit 11, the timings of the operation pulses are adjusted and the adjusted timings are notified to each element, whereby the operation by the timing controller 20 finishes.

Figure 6:
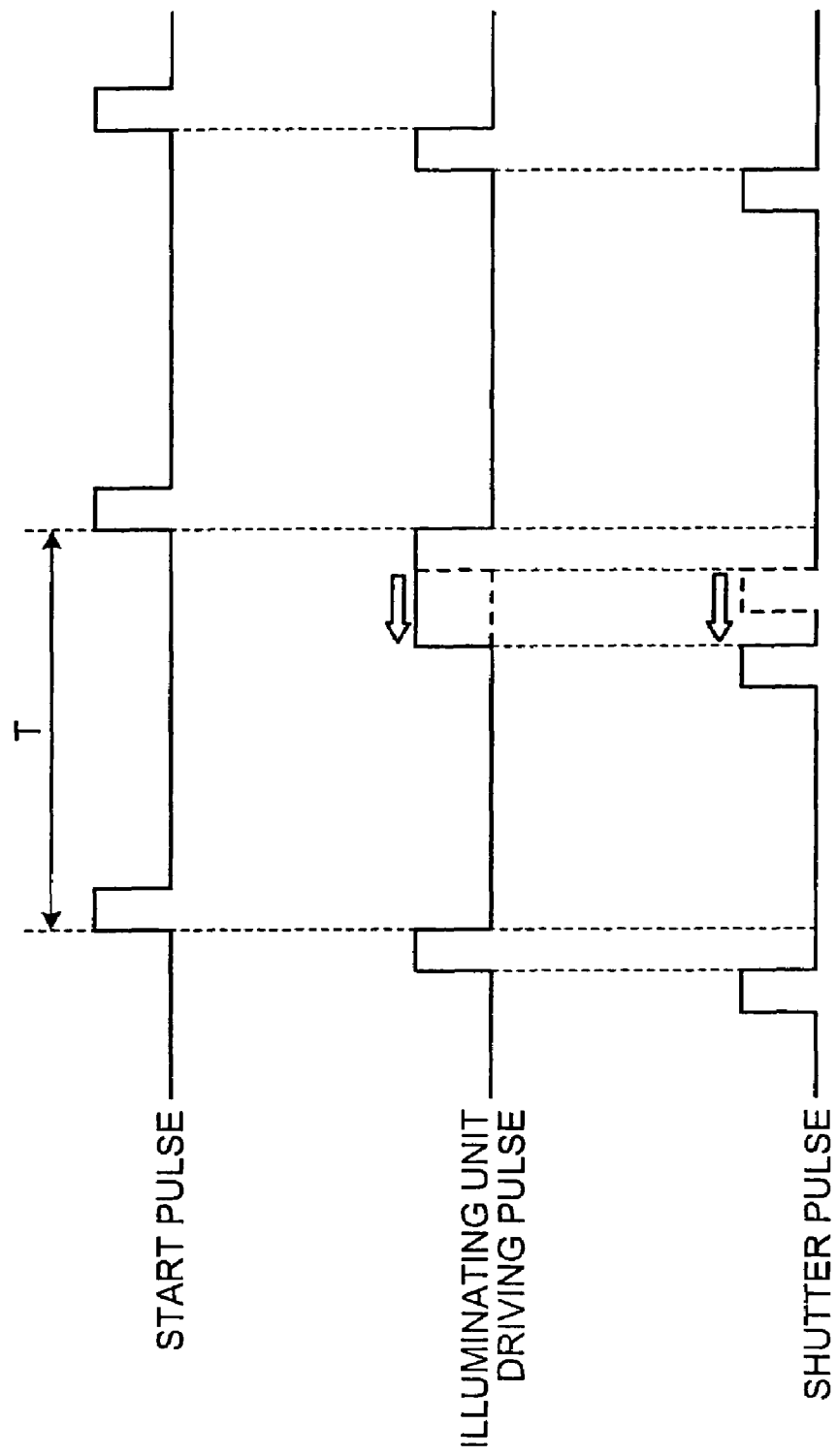
FIG. 6 is a schematic drawing for illustrating an operation of the timing controller.
Figure 7:
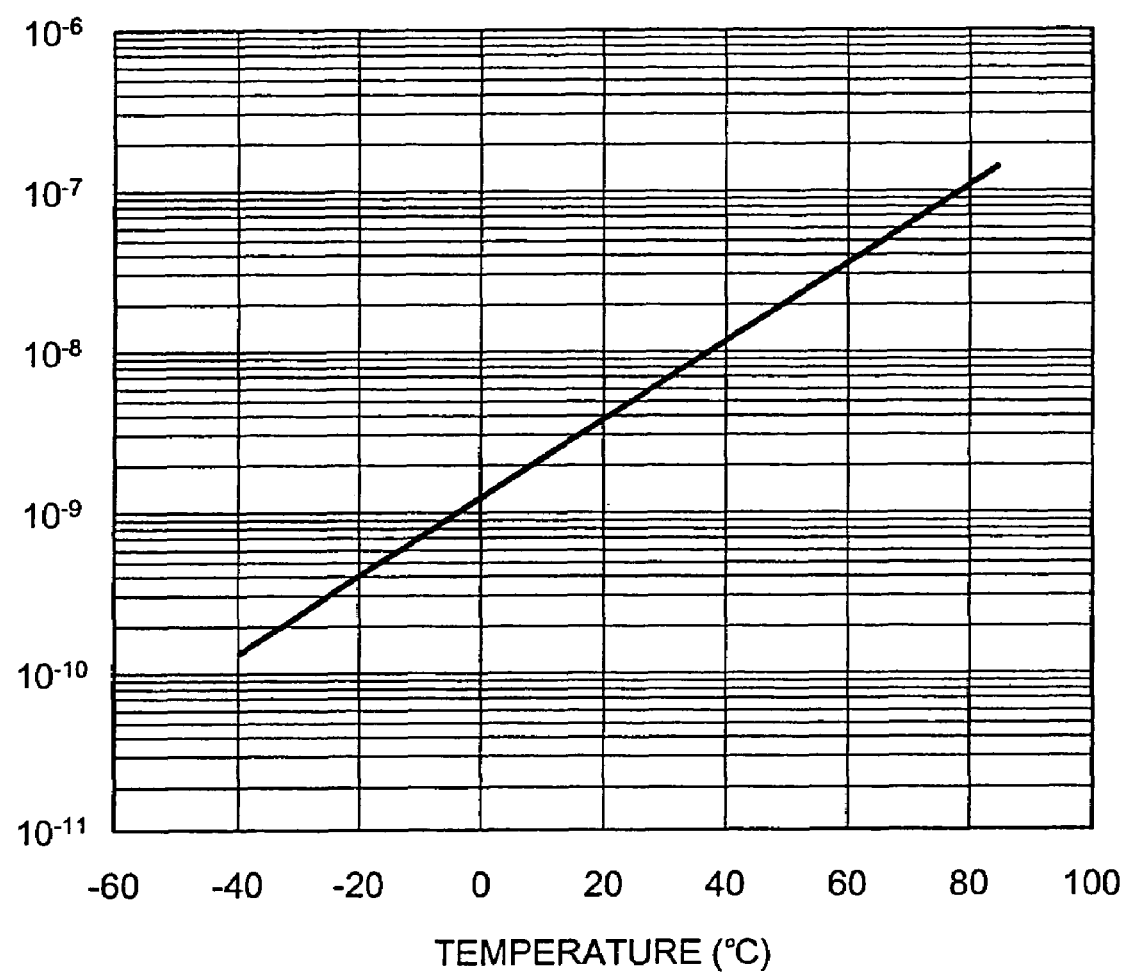
FIG. 7 is a schematic graph of temperature dependency of dark current.

Operations at steps S108 and S109 will be simply described. FIG. 6 is a schematic drawing illustrating how the timings are changed in steps S108 and S109. As described above, in the present embodiment, the light intensity of the illuminating light output by the illuminating unit 11 is changed by adjusting the driving time of the illuminating unit 11; therefore, the pulse width of the illuminating unit driving pulse is changed. More specifically, however, three ways of changing the pulse width of the illuminating unit driving pulse may be considered; firstly to shift only the rising edge of the pulse; secondly to shift only the falling edge of the pulse; and thirdly to shift both the rising edge and the falling edge of the pulse.

Among the plurality of ways of changing the pulse width, the present embodiment adjusts the pulse width at step S108 by shifting only the rising edge of the illuminating unit driving pulse and not the falling edge of the illuminating unit driving pulse. Since the timing controller 20 performs the controlling operation as described above, the start pulses remain to be supplied at fixed timing, in other words, the imaging unit output timing are kept supplied at fixed timing, independent of the change in the pulse width of the illuminating unit driving pulse.

Times the shutter pulse rises and falls change as shown in FIG. 6 due to the control operation in step S109. Specifically, the falling edge of the shutter pulse is shifted according to the shift of the rising edge of the illuminating unit driving pulse in step S108 so that the rising edge of the illuminating unit driving pulse remains coinciding with the falling edge of the shutter pulse, and at the same time, the rising edge of the shutter pulse is shifted corresponding to the shift of the falling edge of the shutter pulse. In the present embodiment, the pulse width of the shutter pulse is fixed regardless of the changes in the pulse width of the illuminating unit driving pulse; therefore, the timing of rise and fall of the shutter pulse is changed by an amount that is equivalent to the amount of change in the timing of rise of the illuminating unit driving pulse.

An advantage of the capsule endoscope system according to the present embodiment will be described. In the capsule endoscope system according to the present embodiment, the charges accumulated due to the dark current are eliminated in the capsule endoscope 2. The elimination of the charges prevents the noise components caused by the dark current from mixing into the picked up image data.

In the present embodiment, the dark current is eliminated (in other words, the shutter pulse is supplied) at least after the imaging unit finishes supplying an output and before the illuminating unit driving pulse is supplied in each imaging period. A reason for setting the aforementioned timing is described hereinafter. It is not preferred from perspective of acquiring a high quality image data to supply the shutter pulse after the illuminating unit driving pulse is supplied, since the charges generated corresponding to the incident light by the photoelectric transducers 25 are, together, eliminated. Hence, in the present embodiment, the shutter pulse is supplied before the illuminating unit driving pulse is supplied, and the noise components can be eliminated, without negatively affecting the charges corresponding to the incident light, by supplying the shutter pulse with the timing described above.

The shutter pulse is generally formed with a high intensity pulse signal. Hence, if the shutter pulses are supplied during the charge transfer by the vertical shift register 27 and the horizontal shift register 28 provided in the solid-state image sensor 24, i.e., if the shutter pulses are supplied during the output of analog electronic signals from the imaging unit 12, the shutter pulse might negatively affect the transfer of the charges. Therefore, in the present embodiment, the shutter pulse is supplied after the output of the analog electronic signals from the imaging unit 12 is finished. When the shutter pulse is supplied with the aforementioned timing, the noise components can be eliminated without negative influence on the transfer of the charges.

In the present embodiment, the supplying timing of the shutter pulse is controlled so that the shutter pulse is supplied right before the illuminating unit driving pulse is supplied, and more preferably the timings are controlled so that the rising edge of the illuminating unit driving pulse coincides with the falling edge of the shutter pulse, as shown in FIGS. 4 and 6. By having the aforementioned supplying timings, the capsule endoscope system according to the present embodiment has an advantage in which the noise components caused by the dark current can be more surely eliminated. Since the charges caused by the dark current are gradually accumulated over the entire imaging period, the noise components caused by the dark current are reaccumulated after the noise components are eliminated by supplying the shutter pulse once. Therefore, in the present embodiment, the shutter pulse falls right before the timing of incidence of the light, which corresponds to the subject interior image, into the photoelectric transducer 25 (i.e., the timing the illuminating unit driving pulse is supplied), and more preferably the shutter pulse falls when the illuminating unit driving pulse rises. Such configuration is advantageous in that the noise components can more surely be eliminated.

Furthermore, in the present embodiment, the output time of the illuminating light output from the illuminating unit 11 is changed based on the comparison result between the image luminance, which is the luminance of the image actually picked up, and the predetermined reference luminance, which is determined by the display property and the like of the display device 4. Therefore, the capsule endoscope 2 according to the present embodiment has an advantage in which a high quality image data having luminance that is similar to the reference luminance can be acquired.

Specifically, in the present embodiment, the comparing unit 18 derives only the magnitude correlation between the image luminance and the reference luminance. Since only the magnitude correlation between the image luminance and the reference luminance is derived as the comparison result used by the light-emission-amount adjustment unit 19, the comparing unit 18 can be formed with a comparator using a so-called operational amplifier (op-amp), a resistor, and the like. Since the comparator has a simple configuration as well as power consumption thereof is suppressed to a low value, a problem such as an increase in size of the capsule endoscope 2 and an increase in power consumption therein can be prevented even if the comparator is installed in the capsule endoscope 2.

Further, the light-emission-amount adjustment unit 19 changes the output time of the illuminating light by a preliminarily determined time ($\Delta t$ in the flowchart of FIG. 5) based on the magnitude correlation acquired by the comparing unit 18. As shown in the flowchart of FIG. 5, the light-emission-amount adjustment unit 19 decreases the output time of the illuminating light by $\Delta t$ when the image luminance exceeds the reference luminance, and the light-emission-amount adjustment unit 19 increases the output time of the illuminating light by $\Delta t$ when the image luminance is below the reference luminance. Consequently, calculation at the light-emission-amount adjustment unit 19 can be reduced as well as a configuration of the electronic circuit and the like for realizing the light-emission-amount adjustment unit 19 can be simplified. Therefore, a miniaturized light-emission-amount adjustment unit 19 with low power consumption can be employed.

The capsule endoscope 2 inserted into the subject 1 and picking up the subject interior image sufficiently endures practical use even if the aforementioned mechanism adjusts emission amount. The amount of the incident light inside the subject 1 generally changes continuously and gradually, instead of changing dynamically, for example, when the capsule endoscope 2 moves out of a room to the outside. Hence, even if the capsule endoscope 2 has the simple configuration, the emission amount corresponding to the change of amount of the incident light can be derived without any problems from practical point of view.

Furthermore, in the present embodiment, the timing controller 20 may also have a simple configuration. As shown in FIGS. 4 and 6, the supplying timing of the start pulse is set so that the start pulse has a fixed period and the falling edge of the illuminating unit driving pulse is made to coincide with the rising edge of the start pulse. Even when the pulse width of the illuminating unit driving pulse is changed, the timing controller 20 maintains coincidence between the rising edge of the illuminating unit driving pulse and the falling edge of the shutter pulse while changing the rising edge of the illuminating unit driving pulse.

Hence, in the present embodiment, the timing controller 20 can sufficiently perform a dynamic control based on the output value of the light-emission-amount adjustment unit 19 only by shifting the rising edge of the illuminating unit driving pulse. The supplying timing of the start pulse is always fixed, and the supplying timing is controlled independent of the output value of the light-emission-amount adjustment unit 19. Further, for example, according to the supplying controlling of the shutter pulse, the pulse width may be preliminarily fixed and the coincidence between the falling edge of the shutter pulse and the rising edge of the illuminating unit driving pulse may be preliminarily set as a condition. When the dynamic controlling is performed under the above conditions, the timing controller 20 can control every timing of rises and falls of the driving pulses only by shifting the rising edge of the illuminating unit driving pulse. Therefore, in the capsule endoscope 2 according to the present embodiment, the controlling operation, which is performed to obtain the aforementioned advantages, of the timing controller 20 can be performed by a simple algorithm, and as a result, the capsule endoscope 2 has an advantage in which the timing controller 20 having a simple configuration and low power consumption can be used.

Hereinbefore, the present invention is described with reference to the embodiment; however, the present invention is not limited thereto, and additional embodiments, modifications, and applications will readily occur to those skilled in the art. For example, the noise components may be eliminated by a configuration other than the configuration in which the timing generator 21 supplies the shutter pulse to eliminate the noise components. In the flowchart shown in FIG. 5, the pulse width of the illuminating unit driving pulse is changed unless the image luminance matches with the reference luminance. However, for example, even when one of the image luminance and the reference luminance is larger than the other, the pulse width of the illuminating unit driving pulse does not have to be changed when the luminance difference is less than or equal to a predetermined threshold, by contriving the configuration of the comparing unit 18.

Furthermore, in the present embodiment, the CCD is used as shown in FIG. 3 as the solid-state image sensor constituting the imaging unit 12; however, the present invention is not limited thereto. For example, a complementary metal oxide semiconductor (CMOS) may be used as the solid-state image sensor. The capsule endoscope may include any imaging element as long as the imaging element has the explicit noise components attributable to the dark current. When the CMOS is used as the imaging unit, it is preferable to use a sample-and-hold circuit instead of the A/D converter 13.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope inserted into a subject and picking up an image inside the subject, comprising:

an illuminating unit that illuminates an interior surface of the subject with illuminating light;

an imaging unit that generates an electronic signal corresponding to incident light and outputs the electronic signal generated;

a noise canceller that eliminates noise charges which are caused by dark current and accumulated in the imaging unit;

a timing controller that controls driving starting timing of the noise canceller to lay within a period after the imaging unit finishes an output operation of the electronic signal, the timing controller matching a driving starting timing of the illuminating unit with a driving stopping timing of the noise canceller;

a comparing unit that compares a predetermined reference luminance with a luminance of the image picked up by the imaging unit; and a light-emission-amount adjustment unit that adjusts an emission amount of the illuminating light output from the illuminating unit based on a comparison result of the comparing unit wherein the comparing unit derives a magnitude correlation between the image luminance and the reference luminance, and the light-emission-amount adjustment unit adjusts a driving period of the illuminating unit so as to decrease the driving period by a predetermined time when the image luminance exceeds the reference luminance, and adjusts the driving period of the illuminating unit so as to increase the driving period by a predetermined time when the image luminance is below the reference luminance.

2. A capsule endoscope inserted into a subject and picking up an image inside the subject, comprising:

an illuminating unit that illuminates an interior surface of the subject with illuminating light;

an imaging unit that generates an electronic signal corresponding to incident light and outputs the electronic signal generated;

a noise canceller that eliminates noise charges which are caused by dark current and accumulated in the imaging unit;

a timing controller that controls driving starting timing of the noise canceller to lay within a period after the imaging unit finishes an output operation of the electronic signal, the timing controller matching a driving starting timing of the illuminating unit with a driving stopping timing of the noise canceller;

a comparing unit that compares a predetermined reference luminance with a luminance of the image picked up by the imaging unit; and a light-emission-amount adjustment unit that adjusts an emission amount of the illuminating light output from the illuminating unit based on a comparison result of the comparing unit wherein the timing controller maintains driving stopping timing of the illuminating unit fixed and changes driving starting timing of the illuminating unit, when a driving period of the illuminating unit is adjusted by the light-emission-amount adjustment unit.

3. A capsule endoscope system, comprising:

a capsule endoscope that is inserted into a subject, the capsule endoscope picking up an image inside the subject and radio transmitting a radio signal including image data, outside of the subject; and a receiving device that receives the radio signal transmitted from the capsule endoscope, wherein the receiving device includes a receiving antenna unit that receives the radio signal transmitted from the capsule endoscope, and an external device that performs a predetermined processing on the radio signal received by the receiving antenna unit, and the capsule endoscope includes an illuminating unit that illuminates an interior surface of the subject with illuminating light, an imaging unit that includes a photoelectric transducer, and outputs an electronic signal corresponding to incident light, a noise canceller that eliminates noise charges which are caused due to dark current and accumulated in the imaging unit, a timing controller that controls driving starting timing of the noise canceller to lay within a period after the imaging unit finishes an output operation of the electronic signal, the timing controller matching a driving starting timing of the illuminating unit with a driving stopping timing of the noise canceller, and a radio unit that transmits the radio signal including the image data picked up by the imaging unit, outside of the subject.

4. The capsule endoscope system according to claim 3, further comprising:

a comparing unit that compares a predetermined reference luminance with a luminance of an image picked up by the imaging unit; and a light-emission-amount adjustment unit that adjusts an emission amount of the illuminating light output from the illuminating unit based on a comparison result by the comparing unit, wherein the timing controller maintains a driving stopping timing of the illuminating unit fixed and changes the driving starting timing of the illuminating unit when a driving period of the illuminating unit is adjusted by the light-emission-amount adjustment unit, while controlling so as to match driving starting timing of the illuminating unit with driving stopping timing of the noise canceller.

* * * * *